US00PP24861P2

(12) United States Plant Patent
Kobayashi

(10) Patent No.: US PP24,861 P2
(45) Date of Patent: Sep. 9, 2014

(54) POINSETTIA PLANT NAMED 'PER2711'

(50) Latin Name: *Euphorbia pulcherrima Willd.*
Varietal Denomination: PER2711

(71) Applicant: Ruth Kobayashi, Carlsbad, CA (US)

(72) Inventor: Ruth Kobayashi, Carlsbad, CA (US)

(73) Assignee: Ecke Ranch B.V., De Lier (NL)

( * ) Notice: Subject to any disclaimer, the term of this patent is extended or adjusted under 35 U.S.C. 154(b) by 3 days.

(21) Appl. No.: 13/694,965

(22) Filed: Jan. 22, 2013

(51) Int. Cl.
*A01H 5/00* (2006.01)

(52) U.S. Cl.
USPC ..... Plt./305

(58) Field of Classification Search
USPC ..... Plt./305
See application file for complete search history.

*Primary Examiner* — Anne Grunberg
(74) *Attorney, Agent, or Firm* — C. A. Whealy

(57) ABSTRACT

A new and distinct cultivar of Poinsettia plant named 'PER2711', characterized by its uniform, upright and mounded plant habit; moderately vigorous growth habit; freely and upright branching habit; dark green-colored leaves; mid-season flowering response; large inflorescences with creamy pale yellow-colored flower bracts; and good post-production longevity.

1 Drawing Sheet

Botanical designation: *Euphorbia pulcherrima* Willd.
Cultivar denomination: 'PER2711'.

BACKGROUND OF THE INVENTION

The present invention relates to a new and distinct cultivar of Poinsettia plant, botanically known as *Euphorbia pulcherrima* Willd., and hereinafter referred to by the name 'PER2711'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant originated is a naturally-occurring whole plant mutation of *Euphorbia pulcherrima* Willd. 'PER1139', disclosed in U.S. Plant Pat. No. 22,180. The new Poinsettia plant was discovered and selected by the Inventor as a single flowering plant from within a population of plants of 'PER1139' in a controlled greenhouse environment in Encinitas, Calif. on Dec. 2, 2010.

Asexual reproduction of the new Poinsettia plant by terminal vegetative cuttings in a controlled greenhouse environment in Encinitas, Calif. since February, 2011 has shown that the unique features of this new Poinsettia plant are stable and reproduced true to type in successive generations of asexual reproduction.

SUMMARY OF THE INVENTION

Plants of the new Poinsettia have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER2711'. These characteristics in combination distinguish 'PER2711' as a new and distinct Poinsettia plant:

1. Uniform, upright and mounded plant habit.

2. Moderately vigorous growth habit.
3. Freely and upright branching habit.
4. Dark green-colored leaves.
5. Mid-season flowering response; under natural season conditions, plants flower in late November in Southern California.
6. Large inflorescences with creamy pale yellow-colored flower bracts.
7. Good post-production longevity.

In side-by-side comparisons conducted in Encinitas, Calif., plants of the new Poinsettia differ primarily from plants of the parent, 'PER1139', in flower bract color as plants of 'PER1139' have dark red-colored flower bracts.

Plants of the new Poinsettia can be compared to plants of the *Euphorbia pulcherrima* Willd. 'PER5506', disclosed in U.S. Plant Pat. No. 20,354. In side-by-side comparisons conducted in Encinitas, Calif., plants of the new Poinsettia differed primarily from plants of 'PER5506' in the following characteristics:

1. Plants of the new Poinsettia were not as vigorous as plants of 'PER5506'.
2. Plants of the new Poinsettia flowered about three days earlier than plants of 'PER5506'.
3. Plants of the new Poinsettia and 'PER5506' differed slightly in flower bract color.

Plants of the new Poinsettia can also be compared to plants of the *Euphorbia pulcherrima* Willd. 'PER10606', disclosed in U.S. Plant Pat. No. 20,351. In side-by-side comparisons conducted in Encinitas, Calif., plants of the new Poinsettia differed primarily from plants of 'PER10606' in the following characteristics:

1. Branching habit of plants of the new Poinsettia was more upright than branching habit of plants of 'PER10606'.
2. Plants of the new Poinsettia flowered about 16 days later than plants of 'PER10606' when grown under natural season conditions.
3. Plants of the new Poinsettia and 'PER10606' differed slightly in flower bract color.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER2711' grown in a container.

The photograph at the top of the sheet is a close-up view of a typical flowering plant of 'PER2711'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 24° C., night temperatures averaged 18° C. and light levels averaged 5,000 foot-candles. Measurements and numerical values represent averages for typical flowering plants. Plants were pinched one time and were 17 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER2711'.

Parentage: Naturally-occurring whole plant mutation of *Euphorbia pulcherrima* Willd. 'PER1139', disclosed in U.S. Plant Pat. No. 22,180.

Propagation:

*Type*.—Terminal vegetative cuttings.

*Time to initiate roots*.—About five to ten days at 20° C. night temperature and 27° C. day temperature.

*Time to produce a rooted young plant*.—About four weeks at 20° C. night temperature and 27° C. day temperature.

*Root description*.—Fibrous; white in color.

Plant description:

*Plant habit and form*.—Uniform, upright and mounded plant habit; inverted triangle; large inflorescences positioned above the foliar plane; moderately vigorous growth habit.

*Plant height*.—About 36 cm.

*Plant diameter or spread*.—About 59 cm.

*Lateral branch description*.—Quantity: Freely branching habit, about seven lateral branches develop after pinching. Length: About 34 cm. Diameter: About 7 mm. Internode length: About 2 cm. Strength: Strong. Texture: Smooth, glabrous. Color: Close to 146B.

*Leaf description*.—Arrangement: Alternate, simple. Length: About 12.8 cm. Width: About 8.6 cm. Shape: Broadly lanceolate, occasionally with shallow lobes. Apex: Acuminate. Base: Rounded to nearly truncate. Margin: Mostly entire, occasionally with shallow lobes. Aspect: Flat. Venation pattern: Pinnate, arcuate. Texture, upper surface: Sparsely pubescent. Texture, lower surface: Pubescent; prominent venation. Color: Developing leaves, upper surface: Close to 137A. Developing leaves, lower surface: Close to 137C. Fully expanded leaves, upper surface: Brighter green than N189A; venation, close to 146B. Fully expanded leaves, lower surface: Close to N137B; venation, close to 146D. Petiole: Length: About 6.8 cm. Diameter: About 3 mm. Texture, upper and lower surfaces: Smooth, glabrous. Color, upper and lower surfaces: Close to 146C.

Inflorescence description:

*Inflorescence type and habit*.—Terminal inflorescences are compound corymbs of cyathia with colored flower bracts subtending the cyathia; inflorescences uniformly positioned above the foliar plane.

*Fragrance*.—None detected.

*Flowering response*.—Mid-season flowering response; under natural season conditions, plants typically flower on November 23 in Southern California; under artificial long nyctoperiod/short photoperiod conditions, plants flower about 8 to 8.5 weeks later.

*Post-production longevity*.—Good post-production longevity; plants of the new Poinsettia maintain good substance and flower bract color for about four weeks under interior conditions; inflorescences persistent.

*Inflorescence diameter*.—About 35 cm.

*Inflorescence height* (*depth*).—About 10.5 cm.

*Flower bracts*.—Quantity per inflorescence: About 18 to 20. Length, largest bracts: About 16.8 cm. Width, largest bracts: About 12.6 cm. Shape: Broadly lanceolate. Apex: Acuminate. Base: Rounded. Margin: Entire. Texture, upper surface: Slightly rugose, glabrous. Texture, lower surface: Smooth, glabrous. Aspect: Mostly horizontal; older bracts, drooping. Venation pattern: Pinnate, arcuate. Color: Developing or transitional bracts, upper surface: Ground color, close to 145C; irregular and random patches, close to 145B; along midvein, close to 141B to 141C. Developing or transitional bracts, lower surface: Close to 145B to 145C. Fully expanded bracts, upper surface: Close to 150D; venation, close to 150D; color does not change with development. Fully expanded bracts, lower surface: Slightly more yellow than 145B to slightly more green than 1D; venation, slightly more yellow than 145B to slightly more green than 1D. Bract petiole: Length: About 4.2 cm. Diameter: About 2.5 mm. Texture, upper and lower surfaces: Smooth, glabrous. Color, upper and lower surfaces: Close to 146D.

*Cyathia*.—Quantity per corymb: About ten to twelve. Length: About 1.2 cm. Width: About 7 mm. Shape: Nearly round. Texture: Smooth, glabrous. Color, immature: Close to 137C. Color, mature: Close to 138A.

*Nectaries*.—Quantity per cyathium: One. Length: About 5 mm. Width: About 3 mm. Shape: Roughly elliptical. Texture: Smooth, glabrous. Color: Close to 13A.

*Peduncles*.—Length: About 4 mm. Diameter: About 2 mm. Strength: Strong. Aspect: Mostly upright. Texture: Smooth, glabrous. Color: Close to 146B to 146C.

*Reproductive organs*.—Stamens: Quantity per cyathium: About ten. Filament length: About 3.5 mm. Filament color: Close to 20D. Anther shape: Oval; bi-lobed. Anther length: About 1 mm. Anther color: Close to 153A. Amount of pollen: Scarce. Pollen color: Close to 153D. Pistils: Pistil development has not been observed on plants of the new Poinsettia.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER2711' as illustrated and described.

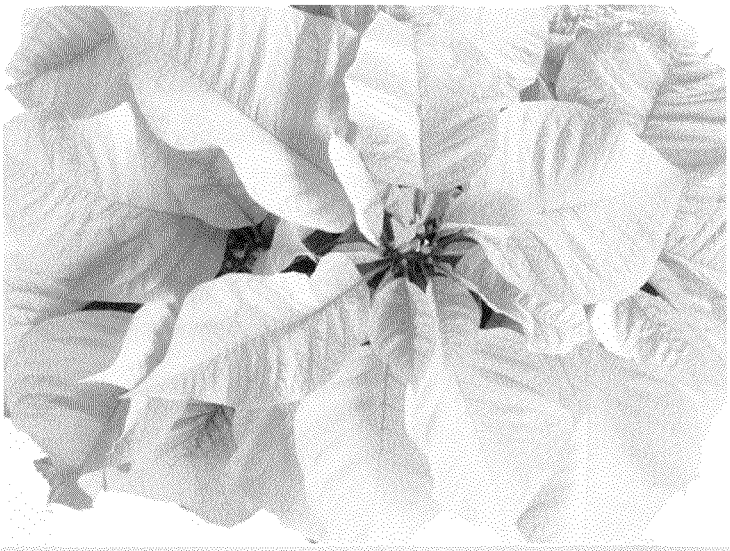
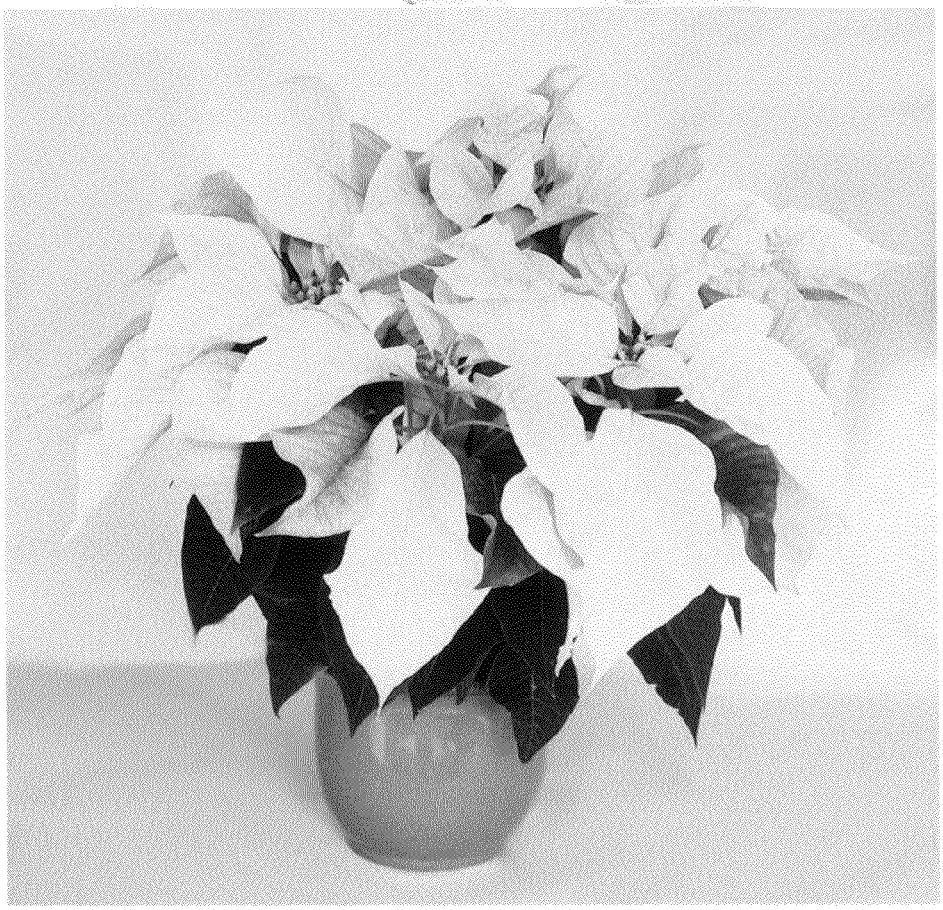

* * * * *